US009078571B2

(12) United States Patent
Bridger et al.

(10) Patent No.: US 9,078,571 B2
(45) Date of Patent: Jul. 14, 2015

(54) HIGH SENSITIVITY NOISE IMMUNE STETHOSCOPE

(75) Inventors: Keith Bridger, Washington, DC (US); Arthur V. Cooke, Baltimore, MD (US); Dennis J. Kohlhafer, Ellicott City, MD (US); Joseph J. Lutian, Arnold, MD (US); John M. Sewell, Glen Rock, PA (US); Richard E. Strite, Germantown, MD (US)

(73) Assignee: Active Signal Technologies, Inc., Linthicum, MD (US)

( * ) Notice: Subject to any disclaimer, the term of this patent is extended or adjusted under 35 U.S.C. 154(b) by 312 days.

(21) Appl. No.: 13/569,835

(22) Filed: Aug. 8, 2012

(65) Prior Publication Data
US 2012/0302920 A1 Nov. 29, 2012

Related U.S. Application Data

(62) Division of application No. 11/599,833, filed on Nov. 15, 2006, now Pat. No. 8,265,291.

(60) Provisional application No. 60/736,914, filed on Nov. 15, 2005.

(51) Int. Cl.
A61B 7/04 (2006.01)
(52) U.S. Cl.
CPC .......................................... A61B 7/04 (2013.01)
(58) Field of Classification Search
CPC ............. A61B 7/04; A61B 7/02; H04R 29/00
USPC ................................ 381/67, 56; 600/528, 586
See application file for complete search history.

(56) References Cited

U.S. PATENT DOCUMENTS

| 3,989,895 A | 11/1976 | O'Daniel, Sr. |
| 4,012,604 A | 3/1977 | Speidel |

(Continued)

FOREIGN PATENT DOCUMENTS

| EP | 1053716 A1 | 11/2000 |
| WO | 0035348 A1 | 6/2000 |
| WO | 0197675 A2 | 12/2001 |

OTHER PUBLICATIONS http://www.allheart.com/nvsd.html; Oct. 27, 2006.
(Continued)

*Primary Examiner* — Disler Paul
(74) *Attorney, Agent, or Firm* — Alan G. Towner, Esq.; Pietragallo Gordon Alfano Bosick & Raspanti, LLP

(57) ABSTRACT

A physiological sensing stethoscope suitable for use in high-noise environments is disclosed. The stethoscope is designed to be substantially matched to the mechanical impedance of monitored physiological activity and substantially mismatched to the mechanical impedance of air-coupled acoustic activity. One embodiment of the stethoscope utilizes a passive acoustic system. Another embodiment utilizes an active Doppler system. The passive and active systems can be combined in one stethoscope enabling switching from a passive mode to an active mode suitable for use in very high-noise environments. The stethoscope is suitable for use in environments having an ambient background noise of 100 dBA and higher. The passive includes a head having a housing, a flexural disc mounted with the housing, and an electromechanical stack positioned between the housing and the flexural disc in contact with the skin of a patient. The active system detects Doppler shifts using a high-frequency transmitter and receiver.

18 Claims, 14 Drawing Sheets

(56) References Cited

U.S. PATENT DOCUMENTS

| | | | |
|---|---|---|---|
| 4,156,800 A | 5/1979 | Sear et al. | |
| 4,195,643 A | 4/1980 | Pratt, Jr. | |
| 4,258,229 A | 3/1981 | Eggert et al. | |
| 4,295,471 A | 10/1981 | Kaspari | |
| 4,326,285 A | 4/1982 | Dieter, Jr. et al. | |
| 4,413,629 A | 11/1983 | Durley, III | |
| 4,692,942 A | 9/1987 | Morgand | |
| 4,770,189 A * | 9/1988 | Shyu | 600/586 |
| 4,784,154 A | 11/1988 | Shirley et al. | |
| 4,821,327 A | 4/1989 | Furugard et al. | |
| 4,989,609 A * | 2/1991 | Smith et al. | 600/454 |
| 5,025,809 A | 6/1991 | Johnson et al. | |
| 5,309,922 A | 5/1994 | Schechter et al. | |
| 5,337,752 A | 8/1994 | Reeves | |
| 5,467,775 A | 11/1995 | Callahan et al. | |
| 5,492,129 A | 2/1996 | Greenberger | |
| 5,497,426 A | 3/1996 | Jay | |
| 5,539,831 A | 7/1996 | Harley | |
| 5,610,987 A | 3/1997 | Harley | |
| 5,638,453 A | 6/1997 | McLaughlin | |
| 5,687,738 A | 11/1997 | Shapiro et al. | |
| 5,812,678 A | 9/1998 | Scalise et al. | |
| 5,827,198 A | 10/1998 | Kassal | |
| 5,848,168 A | 12/1998 | Shipps et al. | |
| 5,852,263 A | 12/1998 | Dieken | |
| 5,909,495 A | 6/1999 | Andrea | |
| 5,919,144 A | 7/1999 | Bridger et al. | |
| 5,960,089 A | 9/1999 | Bouricius et al. | |
| 6,028,942 A | 2/2000 | Greenberger | |
| 6,134,331 A | 10/2000 | Baekgaard | |
| 6,210,334 B1 | 4/2001 | Phillips | |
| 6,226,386 B1 | 5/2001 | Akino | |
| 6,261,238 B1 * | 7/2001 | Gavriely | 600/532 |
| 6,275,594 B1 | 8/2001 | Senoo et al. | |
| 6,278,786 B1 | 8/2001 | McIntosh | |
| 6,295,365 B1 | 9/2001 | Ota | |
| 6,339,719 B1 | 1/2002 | Lee et al. | |
| 6,347,147 B1 | 2/2002 | Downs, Jr. et al. | |
| 6,359,992 B1 * | 3/2002 | Preves et al. | 381/312 |
| 6,366,675 B1 | 4/2002 | Toda | |
| 6,438,238 B1 | 8/2002 | Callahan | |
| 6,487,295 B1 | 11/2002 | Lofgren et al. | |
| 6,491,647 B1 | 12/2002 | Bridger et al. | |
| 6,498,854 B1 | 12/2002 | Smith | |
| 6,587,564 B1 | 7/2003 | Cusson | |
| 6,587,567 B1 | 7/2003 | Yamamoto | |
| 6,661,897 B2 | 12/2003 | Smith | |
| 6,751,954 B2 | 6/2004 | Bridger et al. | |
| 6,887,199 B2 | 5/2005 | Bridger et al. | |
| 7,822,212 B2 * | 10/2010 | Merline et al. | 381/57 |
| 8,548,174 B2 * | 10/2013 | Dufresne et al. | 381/67 |
| 2001/0012792 A1 * | 8/2001 | Murray | 455/567 |
| 2001/0014162 A1 | 8/2001 | Orten | |
| 2003/0208130 A1 | 11/2003 | Yotam et al. | |
| 2006/0056641 A1 * | 3/2006 | Nadjar et al. | 381/67 |
| 2007/0060825 A1 | 3/2007 | Newman et al. | |

OTHER PUBLICATIONS

Vmed Technology, Inc., "Ultrascope Veterinary Doppler Stethoscope.".

* cited by examiner

HIGH SENSITIVITY NOISE IMMUNE STETHOSCOPE

CROSS-REFERENCE TO RELATED APPLICATIONS

This application is a divisional application of U.S. patent application Ser. No. 11/599,833, filed Nov. 15, 2006, which claims the benefit of U. S. Provisional Patent Application Ser. No. 60/736,914 filed Nov. 15, 2005, both of which are incorporated herein by reference.

GOVERNMENT CONTRACT

The United States Government has certain rights to this invention pursuant to Contract No. DAMD17-02-C-0028 awarded by the U.S. Army.

FIELD OF THE INVENTION

The present invention relates generally to a stethoscope, and more particularly, relates to a stethoscope including passive and active modes of auscultation suitable for use in high-noise environments.

BACKGROUND INFORMATION

Among the most critical and challenging medical problems in the emergency medical, and particularly the aeromedical field, is the detection and discrimination of heart and breathing sounds of seriously injured patients in environments having high levels of background noise. During the initial stages of diagnosis and/or treatment, the physician needs to stabilize or maintain each patient's condition. Effective stabilization cannot be accomplished without monitoring the heart and respiration of the patient. Specifically, the patient may be susceptible to shock, which can be detected by monitoring vital signs, including heart rate, respiration and blood pressure. In addition, if the patient has experienced chest trauma, the detection and monitoring of respiration is critical for treating possible lung collapse or conditions causing the lungs to fill with fluid. When this occurs and the patient is intubated effective tube placement and integrity needs to be monitored.

Severely injured patients are often evacuated by helicopter to a remote location for proper treatment. For example, patients injured in the field during combat are often evacuated to a remote treating area by a Blackhawk UH-60 helicopter. Traditional auscultation devices have proved ineffective in accurately monitoring a patient's heart and breathing sounds when high levels of background noise, such as those created by helicopters, are present. Background noise can comprise airborne acoustic waves as well as structure borne sounds and vibrations which couple to the patient's body. The noise level generated by a Blackhawk UH-60 helicopter, for example, can exceed 100 dBA. Conventional acoustic and electronic stethoscopes cannot reliably detect heart sounds or respiration under these conditions, making it impossible to discriminate subtle features in either physiological signal.

The background noise can include discrete frequencies, broadband noise and/or a combination of both. All of these components may be present in varying degrees in high-noise environments such as battlefields and civilian emergency medical services (EMS) sites. Noise can interfere with the physiological sounds a user wishes to hear through a stethoscope because there are several leakage pathways including, through and around the earpieces, through the acoustic tube connecting the earpieces with the stethoscope head (via mechanical coupling), between the stethoscope head and the patient's body, and through the patient's body directly into the stethoscope head via mechanical coupling between a vibrating transport vehicle and the patient's body.

Although passive acoustic stethoscopes can be functional in environments having a background noise of up to about 80 dBA, medical professionals often need to ascertain physiological patient information in environments having higher levels of background noise.

Accordingly, a need remains for a stethoscope having both an acoustic amplifying system and an active Doppler physiological activity detection system that is effective in high background noise environments and overcomes the limitations, disadvantages, or shortcomings of known auscultation devices.

The high acoustic background noise of military and civilian helicopters and other medical transport vehicles require that ear protection be used by treating physicians. Hence the stethoscope earpieces must be integrated in some manner with the ear protection. For example, in the Army, Communication Ear Plugs (CEPs) placed directly into the external ear canal are used to reduce noise leakage from the surrounding air into the ears while directing communication signals into miniature speakers in-situ in the plug. Replacement of the conventional acoustic tube (hollow pipe) of a normal stethoscope with wires in an electronic stethoscope (which has a transducer in place of the bell and diaphragm) provides an electrical connection that eliminates the noise transmitted through the walls of the tube. However, this has no effect on noise leakage pathways at the transducer where the signal is received. Prior art devices using a microphone inside an air-coupled sensor head do not reduce the noise leakage between the head of the stethoscope and the patient's body as both the noise and the signal are amplified.

Accordingly, a need remains for a stethoscope that incorporates the capability to enhance the auscultation of physiological sounds while rejecting ambient noise.

SUMMARY OF THE INVENTION

The present invention is directed to a highly sensitive physiological sensing stethoscope suitable for use in high-noise environments. The stethoscope can comprise components of a passive acoustic amplifying system, an active acoustic Doppler system and preferably components combining the active and passive modalities. The stethoscope is designed to be substantially matched to the impedance of monitored physiological signals and substantially mismatched to the impedance of air-coupled ambient energy, such as ambient background noise. The stethoscope is suitable for use in environments having high ambient background noise, e.g., 95 dBA and higher.

The range of physiological frequencies that are accurately reproduced by the present stethoscope is considerably wider than available from a conventional mechanical bell/diaphragm (air coupled) stethoscope. This extended frequency range is achieved without compromising the signal to noise ratio of the physiological sounds due in part to the impedance match between the transducer and the tissue compared to the poor impedance match inherent to the air-coupled interface.

An aspect of the present invention is to provide a stethoscope comprising a housing including an inner cavity, a flexural disc mounted on the housing structured and arranged to deflect based upon physiological activity of a patient, and an electromechanical stack positioned at least partially within the inner cavity mechanically coupled between the housing and the flexural disc which generates an electrical signal upon deflection of the flexural disc.

Another aspect of the present invention is to provide a stethoscope comprising a housing, an electromechanical stack positioned within the housing, and means for mechanically amplifying physiological signals in communication with the electromechanical stack.

A further aspect of the present invention is to provide a stethoscope comprising a housing having an interior and a longitudinal axis, a transducer capable of converting mechanical energy into an electrical signal positioned within the housing wherein the transducer has a longest dimension substantially collinear with the longitudinal axis, means for mechanically amplifying forces exerted by physiological activity in communication with the transducer, and means for amplifying the electrical signal of the transducer.

Another aspect of the present invention is to provide a stethoscope comprising a housing, a passive system incorporated into the housing, the passive system comprising an acoustic transducer, an active system incorporated into the housing, the active system comprising a transmitter an a receiver, and a switch in communication with the passive system and the active system, the switch able to select the passive system or active system.

A further aspect of the present invention is to provide a stethoscope capable of use in a high amplitude ambient noise environment comprising a housing, an active system incorporated into the housing, the active system comprising a transmitter and a receiver for sending and receiving high frequency signals to and from a patient exposed to the high amplitude ambient noise environment, and a signal conditioner for reducing or eliminating unwanted signals selected from the high amplitude ambient noise and/or other spurious signals.

Another aspect of the present invention is to provide a method for detecting physiological activity in a high amplitude ambient noise environment comprising transmitting a high frequency signal into a patient, receiving a reflected signal, demodulating the reflected signal, filtering the demodulated signal, and transmitting the demodulated and filtered signal to an earpiece.

These and other aspects of the present invention will be more fully understood following a review of this specification and drawings.

DETAILED DESCRIPTION

The present invention is directed to a stethoscope for detection and/or characterization of physiological processes, such as heart and respiration activity, in high-noise environments. As used herein, the term "high-noise environment" means a temporary or sustained ambient background noise of greater than 80 dBA, for example, at least 90 or 100 dBA. High-noise environments can be generated by many sources. For example, emergency rescue vehicles, such as fixed and rotary wing aircraft, and emergency ground transport platforms, such as ambulances may create a high noise environment. High-noise environments may also include military combat zones, general ambient city noise, outdoor accident scenes, emergency rooms and trauma centers.

In environments having a background noise level above 80 dBA, unamplified acoustic stethoscopes are largely ineffective for patient diagnosis. In accordance with an embodiment of the present invention, a "passive" system utilizing amplified acoustics may be used for relatively high-noise environments, e.g., between ~80 dBA and 95 dBA. In accordance with another embodiment of the present invention an "active" system such as Doppler may be employed in environments with very high-noise, e.g., greater than 95 dBA to allow medical personnel to obtain vital patient respiration and pulmonary information. The precise background noise level at which it becomes difficult to discern patient respiration via auscultation varies widely depending on the user. Most stethoscope users find that acoustic stethoscopes become less effective in environments having a background noise above 80 dBA.

In one embodiment, an amplified passive acoustic system can be employed in a stethoscope in accordance with the present invention. In another embodiment, an active Doppler system can be employed in the stethoscope of the present invention. In yet another embodiment, both the passive acoustic system and the active Doppler system can be employed in the stethoscope of the present invention. For example, passive acoustic amplification may be desirable for environments where the noise levels are between 80 and 95 dBA whereas Doppler systems may be desirable for noise levels beyond 95 dBA. An amplified acoustic system may retain much more acoustic information than a Doppler system for purposes of characterization of heart and breath and lung sounds, and uses less power. However, when the ambient noise level is too high, and the physician still needs to know that normal activity is present, the Doppler system may be used.

Figure 1:
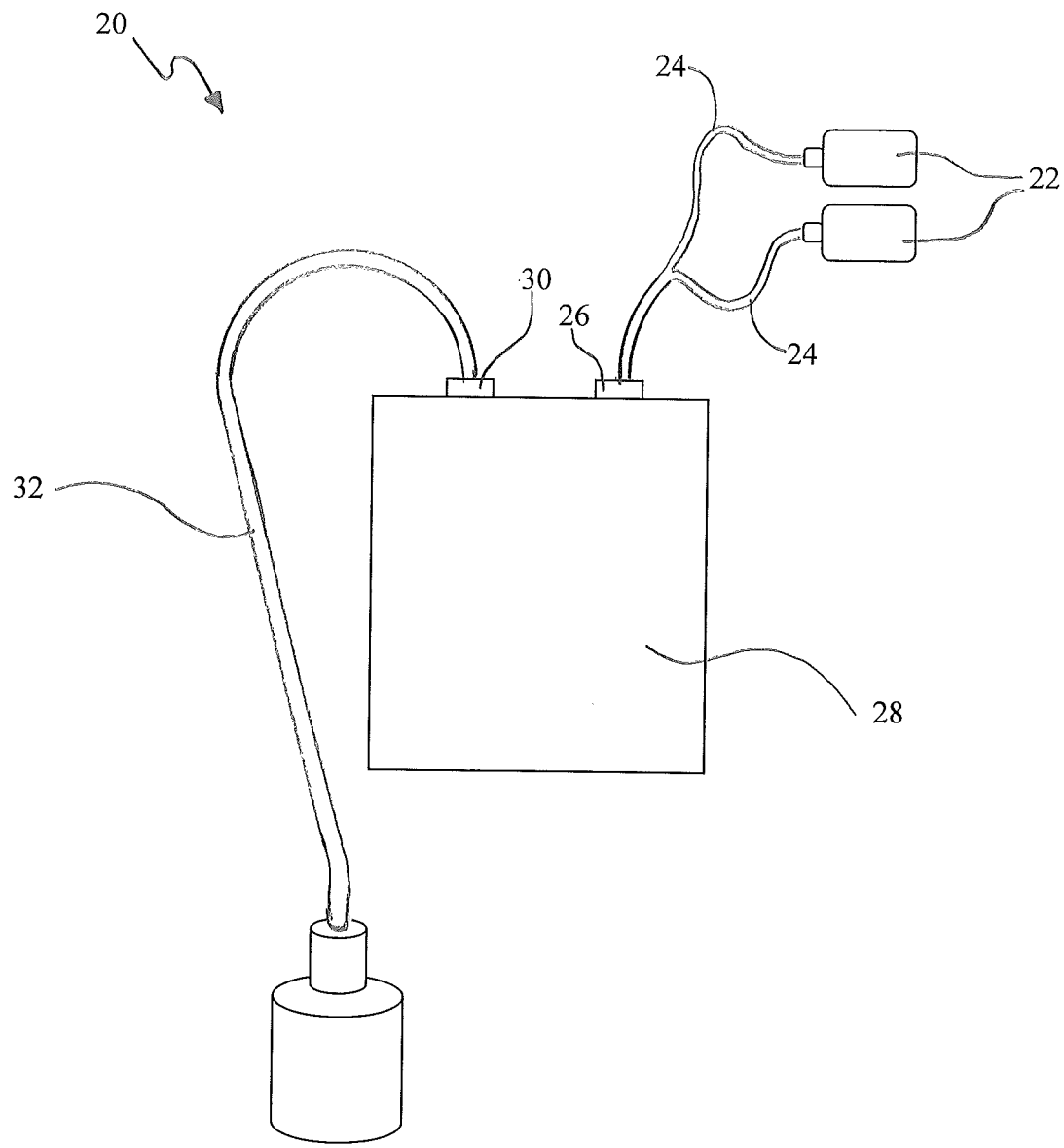
FIG. 1 is a partially schematic view of an integrated stethoscope having a head, an electronics box and earpieces in accordance with an embodiment of the present invention.

As shown in FIG. 1, an integrated stethoscope 20, in accordance with an embodiment of the present invention, comprises a head 34, an electronics box 28 and earpieces 22. The earpieces 22 can comprise any conventionally known earpieces suitable for contact with the ear of a wearer and capable of transmitting audible sound received by the head 34 of the stethoscope 20. The earpieces 22 can be disposed partially within the external ear canal or can contact the exterior of the ear of the wearer or may surround the ear as a cup. In one embodiment, the stethoscope 20 comprises only one earpiece 22. Suitable earpieces include Communication Ear Pieces (CEPs), surround ear-pads, headset ear pads and the like. The earpiece(s) 22 are connected to an earpiece port 26 of the electronic box 28 by any suitable earpiece connection cable 24. The electronics box 28 may comprise any suitable housing and signal amplifying, filtering, and/or processing boards capable of acquiring physiological signals from the stethoscope head 34 and transmitting audible sound wave signals to the earpiece(s) 22, as will be discussed herein. The electronics box 28 can filter and amplify signals received by the head 34, control the volume and frequency of the received signals, control earpiece power, and the like. The electronics box 28 comprises a head receiving port 30 capable of receiving the electrical signals from the stethoscope head 34 that are transmitted along any suitable head connection cable 32. It may also contain the drivers for Doppler system. In a preferred embodiment, the electronics and battery are mounted in the stethoscope head.

The head 34 of the stethoscope may have at least one surface that is capable of contacting the skin of a patient. In one embodiment, the stethoscope head 34 is structured to receive sound waves produced by physiological processes of a patient, such as heart sounds and breath sounds. In another embodiment, the stethoscope head is structured to transmit ultrasound and receive reflections from anatomical structures such as the heart and lungs. The signal processing converts motion of these structures into audible signals as will be discussed herein. As used herein, the term "patient" can include adult, youth and infant humans as well as animals.

Figure 2:
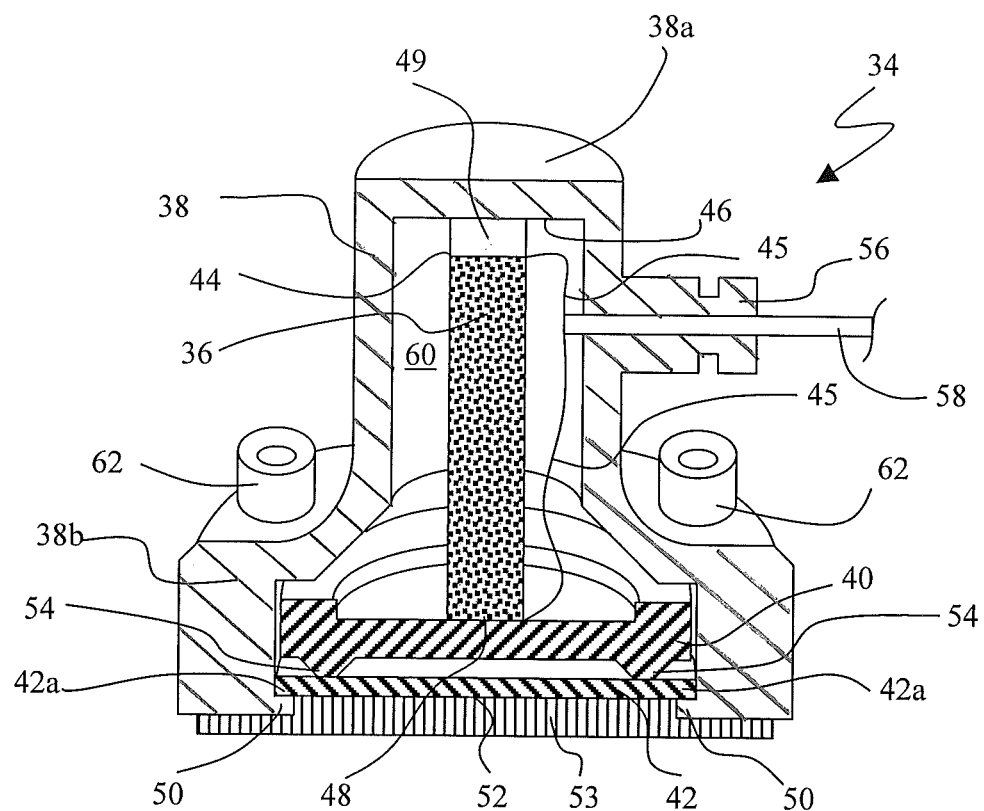
FIG. 2 is a partially schematic side sectional view of a stethoscope head in accordance with an embodiment of the present invention.

In one passive acoustic embodiment, as shown in FIG. 2, the acoustic elements of the stethoscope head 34 comprise an electromechanical stack 36 disposed at least partially within the interior 60 of the housing 38. The interior 60 can be hollow or filled with a compressible material such as foam. The electromechanical stack 36 comprises one or more electromechanical materials. As used herein, the term "electromechanical material" means a material that, when activated, produces electrical energy. As used herein, the term "activated" means that an external mechanical force is applied to the electromechanical material to distort, deform, compress or extend the electromechanical material.

In one embodiment, a first end 44 of the electromechanical stack 36 is restrained against an interior surface 46 of the housing 38, and a second end 48 of the electromechanical stack 36 is engageable with a moveable piston 40 which may constitute part of a mechanical amplifier that is responsive to physiological signals, such as heart sounds and/or respiration, of a patient. A flexural disc 42 is mounted on the housing 38 in contact with the piston 40. As shown in FIG. 2, the electromechanical stack may optionally be terminated at an end 44 with a end-piece such as a rubber damper 49 to minimize transmission of mechanical energy from the environment through housing end 38a into the electromechanical stack 36. As used herein, the term "responsive" means the mechanical amplifier, which may comprise the moveable piston 40, fulcrums 48 and coupling or flexural disc 42, transmits an external mechanical force to the electromechanical stack 36 that correlates to the physiological processes of a patient. For example, the responsive moveable piston 40 and/or flexural disc 42 can activate the electromechanical stack 36 by transferring the mechanical energy produced, for example, by the contraction of muscles of the heart of the patient and/or the rush of air through a patient's airway and lungs during respiration, as will be described herein. The flexural disc 42 can have an exterior surface 52 that is shaped to enhance contact with the skin of a patient to allow for responsive communication between the patient and the stethoscope head 34. Optionally, an interface layer 53 may be inserted between the coupling disc and the patient's skin to enhance contact and acoustical transmission, provide a chemical and moisture barrier layer and minimize patient discomfort. Suitable example materials for this layer include polyurethane and acrylonitrile butadiene styrene (ABS).

Figure 3:
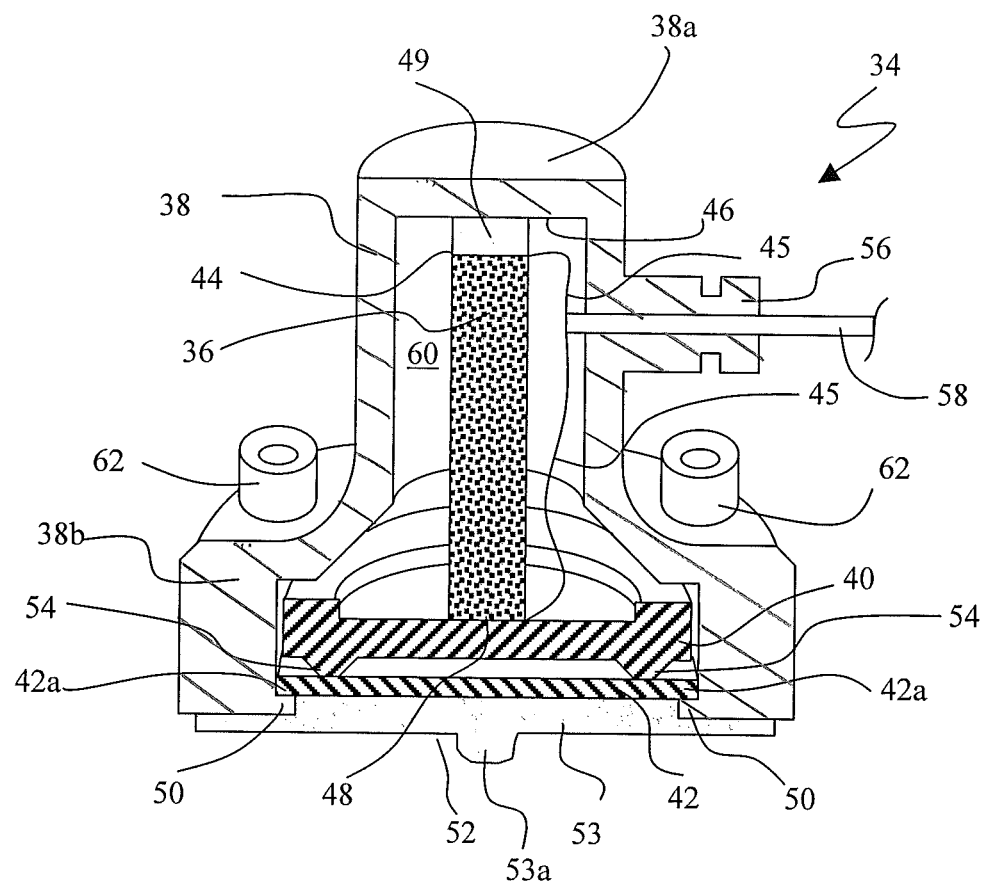
FIG. 3 is a partially schematic side sectional view of a stethoscope head in accordance with an embodiment of the present invention.

As shown in FIG. 3, the interface layer 53 can comprise a protrusion or nipple 53a located at about the center of the interface layer 53 to aid in the transmission of physiological signals when the stethoscope is placed on certain areas of the patient such as, for example, the intercostal space between the ribs.

The enhanced performance of the presently described stethoscope in both high-noise and normal ambient noise environments is achieved through a combination of design features that maximize input signal strength from the physiological source under scrutiny and concurrently maximize the rejection of competing non-physiological signals from the environment. One such feature is a relatively high mass housing as compared to most commercially available stethoscopes. In an embodiment of the present invention, the housing may have a mass greater than 50 to 100 grams. In another embodiment, the housing may have a mass at least half the mass of the total weight of the head of the stethoscope, for example the housing may be 75% by weight of the stethoscope head. For any incoming acoustic signal or vibration, this, serves as an inertial mass at the back end of the electromechanical stack and thereby constitutes a good mechanical ground. Thus, only the front face of the stack (and hence the mechanical system ahead of the stack) will deflect dynamically in response to an input mechanical vibration at the patient face of the stethoscope. At the same time, the heavy housing provides the same inertial mass to the ambient airborne sounds, i.e., it will not be excited by these noises due to its high mechanical impedance, thereby rejecting the ambient noise. In short, the mass of the system greatly improves the coupling of the physiological sounds while just as effectively rejecting the ambient noise, providing a highly enhanced signal to noise ratio.

Other beneficial features include the material parameters and mechanism that provide a transition between the very high mechanical impedance of a typical electromechanical stack and the very low mechanical impedance of human tissue. A mechanical amplification mechanism as shown in FIG. 2 may be used to amplify a very low force while reducing the displacement available from the physiological process in order to produce a greater signal from the stiff electromechanical stack. This is achieved with a lever mechanism comprising the flexural disc 42 supported at its periphery 42a on a rim 50 of the housing 38 and contacted with an annular contact ridge 54 of the piston 40. As used herein, the terms flex, flexible, and deflection imply variable deflection over time. The annular protrusion 50 may be a radially, inwardly, extending rim of the housing 38. This rim 50 retains the flexural disc 42 within the housing 38 while providing a leverage point to counter the force acting on the fulcrum 54. The above referenced transition is also improved by reducing the stiffness of the stack through use of a sensing element with a high aspect ratio. The higher the length to footprint ratio is, the more compliant the stack or element is, enabling the mechanical impedance of the stack to improve relative to the physiology target the stethoscope is monitoring. The stiffness of the stack still remains high relative to the latter, but the gain that is achieved through aspect ratio helps optimize the transition between stiff ceramic and physiological sounds.

A benefit deriving from such a design is that the range of physiological frequencies that are accurately reproduced by the present stethoscope is considerably wider than what is available from a conventional mechanical bell/diaphragm (air coupled) stethoscope or a conventional amplified or electronic stethoscope. This extended frequency range is achieved in part by having the electronic signal transducer mechanical impedance matched to the impedance of the body tissues being monitored. This impedance match improves both the fidelity of the body sounds being amplified and the rejection of air borne interference. The design of the electronic amplifier following the transducer places no limit on the frequency range or fidelity of the biological sounds. The result is a stethoscope that allows a physician to easily hear and identify sounds that were previously difficult or impossible to resolve with current stethoscope technology.

Although the effective stiffness of the stack may be reduced through appropriate changes in element geometry, the beneficial properties of the inherently stiff ceramic stack are retained. The stack offers high electromechanical coupling coefficient and high capacitance. In addition to rejecting platform noise, e.g., from helicopter or ambulance, an advantage of the present invention to optimize coupling between the physiological (mechanical) input signals and the electrical output signal. The coupling path is divided into two principal steps: mechanical coupling between human tissue and the electromechanical element; and the mechanical to electric coupling of the element itself. The latter is defined by the so-called coupling coefficient, k, of the electromechanical material, where:

$$k^2 = [\text{mechanical energy converted to electrical energy}]/[\text{input mechanical energy}]$$

The electromechanical element will have a preferred orientation, or poling direction, which is preset and permanent within limits in the case of piezoelectric materials, or maintained by external bias, using dc electric field in the case of electrostrictive materials, and magnetic field, e.g., with embedded permanent magnets, for magnetostrictive materials. For sensing applications the induced voltage from the electromechanical element is picked-up either by electrodes attached to faces at opposite ends of the poled direction in the material, or in case of magnetostrictive elements by a coil surrounding the material with its longitudinal axis coincident with the poling direction.

In mathematical treatments of electromechanical phenomena the poled direction (z) is referred to by the subscript 3, and the transverse directions (x, y) by the subscripts 1 and 2. Thus when a stress is applied in the 3 direction and the induced voltage is detected on electrodes at opposite ends of the 3 direction, the material coupling coefficient is represented by $k_{33}$ and its piezoelectric voltage coefficient by $g_{33}$. Likewise, when the stress is applied in a transverse direction the voltage at the electrodes on opposite ends of the poled length will be represented by coefficients $k_{31}$ and $g_{31}$. For most materials $k_{33} > k_{31}$ and $g_{33} > g_{31}$, and so the most effective electromechanical coupling and sensing is achieved when the stress and induced electric field (poled direction) are collinear. This case is often referred to as the 33-mode, and in some cases the thickness mode, and is the preferred mode used in an embodiment of this invention.

The mechanical coupling between human tissue and sensor may be thought of as analogous to impedance matching in electrical circuits, except the impedances are mechanical and mostly governed by material stiffness. The electromechanical materials typically have high elastic moduli so that large forces are required to generate strains capable of producing measurable voltages across a solid piece of material. In the case of a block of electromechanical material contacting human tissue, most of the energy from a physiological sound would compress the tissue at the interface and then reflect away from the far stiffer block. Little would be coupled to the block to produce a voltage. Piezoelectric polymers have lower moduli and so can be used to enhance mechanical coupling between tissue and sensor, however the coupling coefficients of these materials are much lower than the stiffer single-crystal or ceramic piezoelectric and electrostrictive materials.

One conventional approach to increasing the mechanical coupling is to form the electromechanical material into long thin strips or plates and mount them as cantilevers or diaphragms. Such an electromechanical element contacting human tissue is far more compliant than the stiff block since the physiological sound now tends to bend the thin element rather than directly compress it. However, these designs all utilize the 31-mode and so will have lower electromechanical coupling than the 33-mode design described herein and are more susceptible to breakage in service. An objective of this invention is thus to use an electromechanical element in its 33-mode and to provide a coupling mechanism that will effectively match the mechanical impedance of the element to that of human tissue at the front face while providing a large impedance mismatch between the outer face and air to reject ambient noise. While monolithic materials and simple compressive or tensile stresses are primarily described herein, it is also recognized that similar benefits may be obtainable by utilizing a composite electromechanical element, and that high coupling coefficients can also be obtained using the shear mode as is done in commercial accelerometers.

As shown in FIGS. 2-3, the electromechanical stack 36 can comprise a monolith or single piece of electromechanical material. In one embodiment, the electromechanical stack 36 has a mass of from about 0.5 grams to about 2 grams, a length (height) of from about 10 mm to about 25 mm, and a width (thickness) of from about 2 mm to about 4 mm. In one embodiment, the head 34 comprises an electromechanical stack 36 having a length that is from about 2 to about 6 times greater than the width.

Example electromechanical materials include piezoelectric materials, electrostrictive and magnetostrictive materials. Suitable piezoelectric materials include piezoelectric lead zirconate titanate (PZT), quartz crystal, lithium niobates, barium titanate, lead titanate, lead meta-niobate, lead magnesium niobate and/or polymeric materials such as polyvinylidene di-fluoride (PVDF). In one embodiment, PZT can be used as an electromechanical material because of high electromechanical coupling values and low cost. Suitable magnetostrictive materials include Terfenol-D, commercially available from Etrema Products, Inc., Ames, Iowa.

The electromechanical stack 36 can be substantially matched to the impedance of physiological signals of a patient, and substantially mismatched to the impedance of air-carried environmental noise since the former is >2 orders of magnitude greater than the latter. The material(s) comprising the electromechanical stack 36 may be selected to exhibit high mechanical impedance, (i.e., a high force to velocity ratio is required to compress it, relative to human tissue and air (which has even lower mechanical impedance). By selecting materials that have high mechanical impedance for the electromechanical stack 36, and contacting the body through a front end mechanical amplifier, energy transferred to the stethoscope head 34 from physiological processes within the patient's body are more readily transferred to the electromechanical stack than energy in the form of ambient background noise propagated through the air that impinges on the head 34 of the stethoscope 20. Accordingly, the stethoscope head 34 can reduce the contribution of acoustic noise in the signal transmitted to the electronics box 28, shown in FIG. 1. What is occurring in this matching is that the impedance combination of the mechanical elements and the stack are designed to be as close to the impedance of the physiological load as possible, yielding a maximum signal input from the physiological excitations. Since most electromechanical materials are far stiffer than human tissue, they are not typically well matched to its motion. In order to enhance physiological signals and reject ambient noise, a force amplifying design can be incorporated into the sensor. Mechanical amplification can be used to improve the impedance match between living tissue (muscle, fat, skin, etc.) and the electromechanical stack 36. In one embodiment, a moveable piston 40 and a flexural disc 42 can be circumferentially mounted within the housing 38. The electromechanical stack 36 can be positioned between the interior surface 46 of the housing 38 and at least a portion of the moveable piston 40. The moveable piston 40 and flexural disc 42 can mechanically amplify the physiological signals of the patient into a higher force or impedance when transferred to the electromechanical stack 36.

Examples of suitable materials for the moveable piston 40 include materials such as aluminum, other metals and composites. In one embodiment, the moveable piston 40 can have a substantially circular cross-section and at least a portion of the moveable piston 40 can contact the flexural disc 42. As shown in FIGS. 2-3, the moveable piston 40 can comprise a contact ridge 54 positioned proximate to the periphery of the moveable piston 40 and extending toward a surface of the flexural disc 42. The contact ridge 54 is capable of engaging the flexural disc 42 when the mechanical force is applied to the flexural disc 42. The contact ridge 54 can comprise a continuous circular ring or a plurality of discrete contact points that are engageable around the periphery of the coupling disc 42 when the electromechanical stack 36 is activated. In one embodiment, the diameter of the moveable piston 40 that contacts the coupling disc 42 is from about 5 mm to about 15 mm.

In one embodiment, the mechanical amplifier is a simple lever mechanism where the larger center portion of the flexural disc 42 deflects against the retaining edge of the housing 38 using the contact ridge 54 as a fulcrum, generating an amplification of the force applied to the disc from the human tissue to be coupled to the stack. Although the moveable piston 40 allows for improved impedance matching between the physiological activity and the electromechanical stack 36, the coupling path of the physiological signal is still stiff enough, i.e., there is sufficient impedance mismatch, between the low impedance characteristic of air and the high impedance electromechanical stack 36, that air-carried ambient background noise will not readily couple to the electromechanical stack 36. Accordingly, air carried noise impinging on the head 34 will be substantially rejected.

As shown in FIGS. 2-3, the flexural disc 42 may be captured within the housing 38 by an overlapping restraining edge 50. The restraining edge 50 can confine the outer periphery 42a of the flexural disc 42 within the housing 38. In one embodiment, the restraining edge 50 overlaps the coupling disc periphery 42a such that the amplifications is ~5 to 1. The design of the flexural disc 42 is determined by the optimum combination of dimensions and material modulus to provide a mechanism that is stiff enough, i.e., impedance mismatched, to resist transferring most air-carried noise, but compliant enough to flex under the influence of physiological displacements. Some examples of suitable materials for the flexural disc 42 include steel, aluminum, composites and the like. The exterior surface 52 of the flexural disc 42 can directly contact a patient's skin and, in use, the responsive coupling disc 42 can convey small mechanical forces to the moveable piston 40 through engaged contact with the contact ridge 54. The contact ridge 54 of the moveable piston 40 can generate a force amplification of the physiological signal transferred from the flexural disc 42.

In order to further improve the impedance matching of the head 34 to the physiological processes of the patient, the exterior surface 52 of the flexural disc 42 can be constructed to allow for direct coupling of the patient's skin to the flexural disc 42 with no air cavity between. Skin directly excites the flexural disc 42, moveable piston 40 and electromechanical stack 36 of the head 34 with a greater force and fidelity than it could with an air interface formed between the flexural disc 42 and the patient's skin. Accordingly, such a configuration provides a greater signal to noise ratio and bandwidth. Amplification and processing of the received acoustic energy is efficient with direct contact between the patient's skin and the flexural disc 42 because the pressure wave received by the flexural disc 42 can be converted directly into electrical signals without loss to air. The configuration eliminates the need of conventional "electronic" stethoscopes, comprising an air cavity adjacent a patient's skin and a microphone pick-up, to pass sound through a second lossy interface at the air to microphone transduction stage.

The transferred amplified force from the flexural disc 42 and moveable piston 40 can then compress the electromechanical stack 36 between the interior surface 46 of the housing 38 and at least a portion of the moveable piston 40. When the electromechanical stack 36 is compressed, an electric charge is produced. The produced electric charge is transferred along wires 45 to a lead 58 which can be connected to the head connection cable 32 of FIG. 1. In one embodiment, the housing 38 can comprise a single outer shell or a plurality of housing pieces 38a and 38b which can be held together by a plurality of fasteners 62. The housing 38 can comprise a removable end cap 38B which can allow for easier assembly of the components within the housing 38. Any suitable fastener 62 can be used to join the housing pieces 38a and 38b, such as rivets, pins, screws, and the like.

Figure 4:
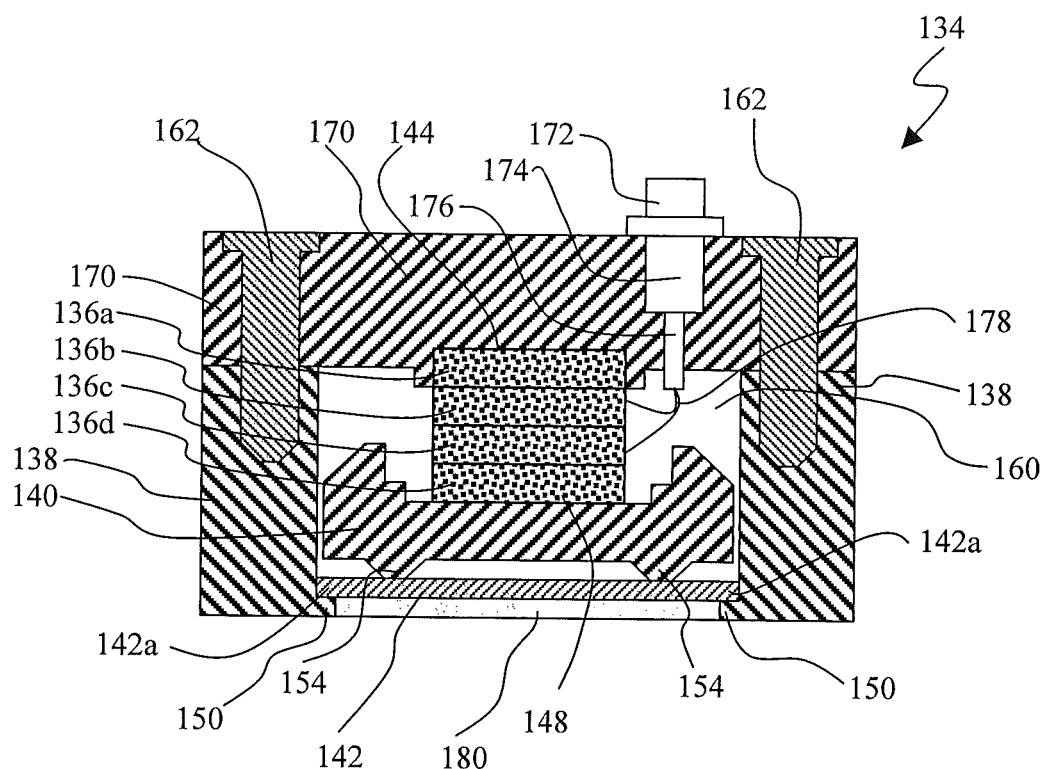
FIG. 4 is a partially schematic side sectional view of a stethoscope head in accordance with an embodiment of the present invention.

In another embodiment of the passive device, shown in FIG. 4, the head 134 can comprise an electromechanical stack comprising a plurality of plates of electromechanical material(s) 136a, 136b, 136c, 136d disposed within the interior 160 of the housing 138. In one embodiment, two or more plates 136a and 136b can comprise the electromechanical stack.

As shown in FIG. 4, the coupling or flexural disc 142 can be restrained within the housing 138 by restraining edge 150 at the outer periphery of the flexural disc 142a. In order to reduce the possible air space between the patient's skin and the flexural disc 142, an interface layer, shown in FIG. 2 as layer 53 and FIG. 3 as layer 53 with protrusion 53a, can include a potting compound layer 180 and can be positioned adjacent the flexural disc 142 as shown. In this embodiment, the outer surface 182 of the potting compound directly contacts the patient's skin. The potting compound can comprise any suitable material sufficiently flexible to transfer energy from the patient to the flexural disc 142 without significant signal dissipation. Suitable potting compounds include low durometer urethane, silicone rubber, or other similar material. In one embodiment, the outer surface 182 of the potting compound layer 180 can comprise a plurality of small dimples to allow improved contact with the skin of the patient. As described above, the moveable piston 140 can contact the flexural disc 142 along a contact ridge 154 to further amplify the physiological processes of the patient. A first end 144 of the first plate 136a in the electromechanical stack can be restrained against a surface of an end cap 170 secured to the housing 138 by a plurality of fasteners 162, and a second end 148 of the last plate 136d in the electromechanical stack can be engageable with the moveable piston 140. When the electromechanical stack 136a, 136b, 136c and 136d is activated, electrical leads 178 connected to one or more of the plates 136a, 136b, 136c and 136d allow an electrical charge generated by the electromechanical stack to be directed through the interior 160 of the housing 138 via the conduit 176 through the end cap 170 and via connector 174 which is in electrical communication with a communication port 172 for electrically engaging head receiving port 30 for FIG. 1.

In the passive mode the electronics in the electronic box 28 in communication with the acoustic transducer amplify the sounds from the patient while substantially maintaining fidelity. Any suitable acoustic sound amplification system conventionally employed in stethoscopes can be used to receive and condition the audio frequency from the mechanical to electrical transducer.

Figure 5:
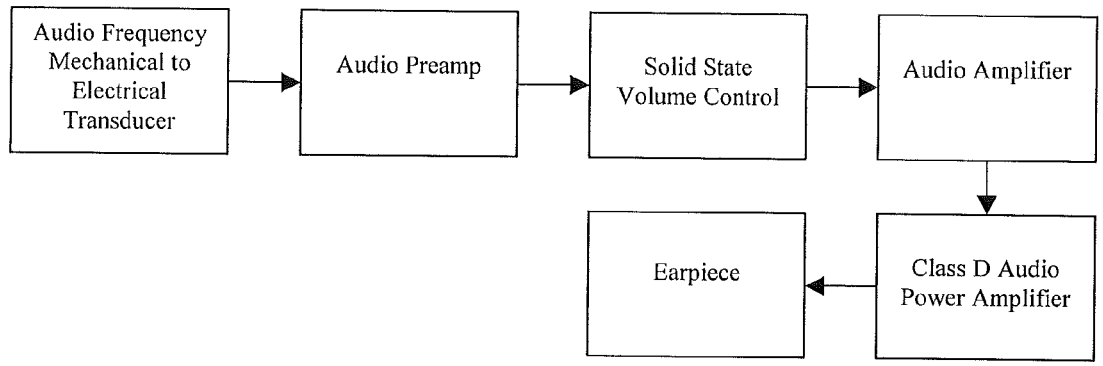
FIG. 5 is a schematic diagram illustrating electronics in communication with an acoustic transducer in accordance with an embodiment of the present invention.

In one embodiment, the audio preamplifier can be matched to the electrical impedance of the mechanical to electrical transducer to provide a gain stage and substantially match the signal impedance to the following functions shown in FIG. 5. A volume control can provide a user selectable control of the volume, such as from zero to maximum gain. In one embodiment, the audio amplifier can include a fixed gain stage which amplifies the signal transmitted to a power amplifier such as a Class D power amplifier designed to provide up to 1 watt of output power while maintaining high efficiency and high fidelity.

Figure 6:
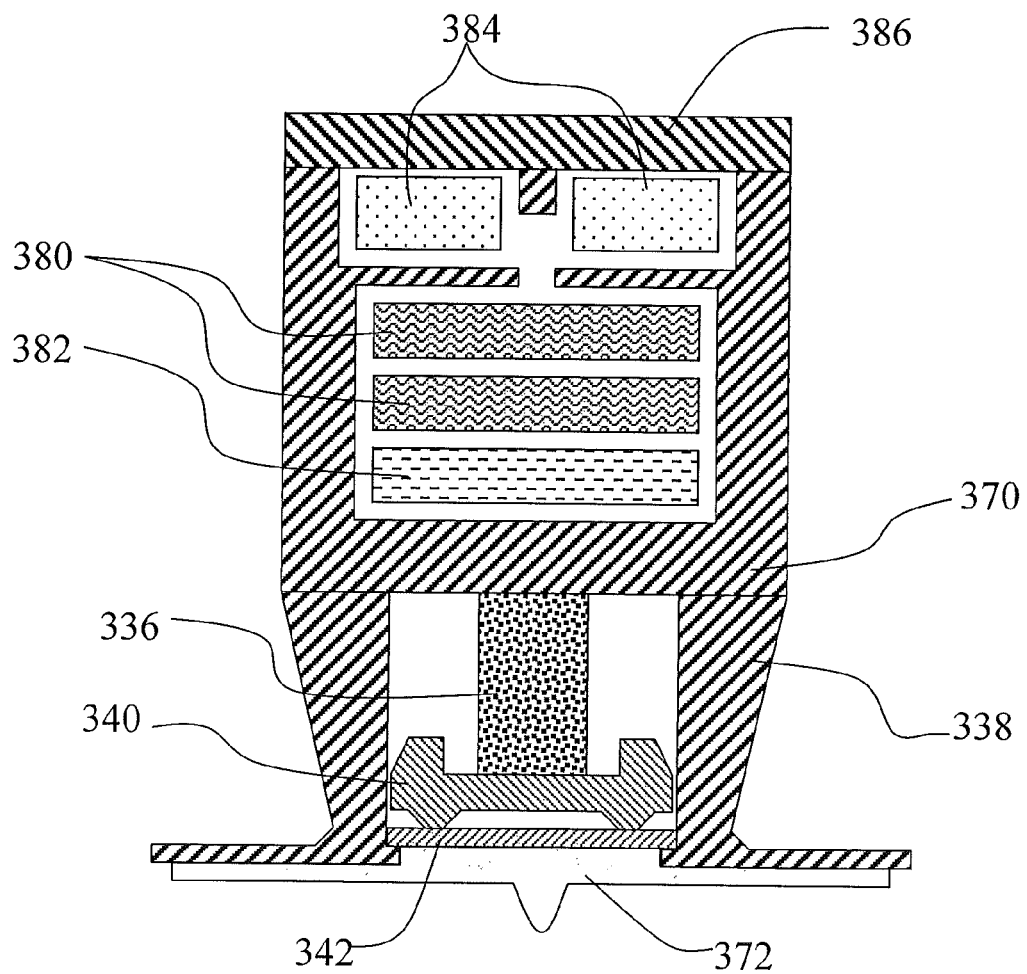
FIG. 6 is a partially schematic side sectional view of a stethoscope head in accordance with an embodiment of the present invention.

In another embodiment of the passive device, as shown in FIG. 6, the stethoscope 320 comprises a housing 338 which contains the stethoscope head, shown in FIG. 1 as head 34, and the electronics box, shown in FIG. 1 as electronics box 28. In this embodiment, the stethoscope 320 can be easier to manipulate by the physician. The stethoscope 320 comprises an electromechanical stack 336 having a first end restrained by a base plate 370 and a second end engageable with a moveable piston 340. The moveable piston 340 can engage a coupling disc 342, and a potting compound layer 372 can be positioned adjacent the coupling disc 342. An electronic amplifier board 382 and at least one signal processing board 380 can be included in the stethoscope 320 in electrical communication (not shown) with the electric charge produced by the compression of the electromechanical stack 336 when activated by the moveable piston 340 and/or coupling disc 342. Batteries 384 or any other suitable power supply can be included to provide power to the electronics amplifier board 382 and/or signal processing board 380. A removable cover 386 can be positioned within the housing 338 to allow for the exchange of a power supply. Earpieces and electrical connections to earpieces (not shown) can also be included in the stethoscope 320.

As described above, another aspect of the present invention is an active acoustic Doppler mode stethoscope when auscultation of physiological sounds using the passive acoustic stethoscope becomes impossible in competition with ambient noise, e.g., when noise levels exceed 95 dBA. The Doppler mode provides active interrogation in a frequency band (typically greater than 1 MHz) well above background sounds typical in high noise environments and thus avoids any issue of overlap or interference. In this embodiment, motion of the lung pleura and heart muscle and vessel walls can be detected well enough to readily assess the functioning of the respiratory and cardiovascular systems in the presence of background noise.

The basic Doppler effect for sound operates on the principle that when a source of sound and a receiver of sound move in relation to each other, the pitch or frequency of the sound perceived or detected at the receiver is different from the pitch or frequency of the source. The Doppler effect is also produced in echoes, when sound or ultrasound is reflected by, or bounced off of, a moving object. Anatomical structures within a patient, such as the heart or lung, reflect ultrasound waves from their walls where an acoustic impedance mismatch occurs and the velocity of the motion determines the frequency of the echoed ultrasound waves. Accordingly, detecting frequency of the echoed ultrasound waves can be used to measure heart and lung activity. Ultrasound is sound with a frequency greater than the upper limit of human hearing, this limit being approximately 20 kHz, for example 1 to 5 MHz for many devices.

In an embodiment utilizing the Doppler mode of the stethoscope of the present invention, ultrasound signals transmitted into the body from the head of the stethoscope are reflected by heart or lung activity within the patient and shifted in frequency compared to the transmitted frequency. The reflected ultrasound waves can be detected by a receiver in the stethoscope head that converts the ultrasound waves into electrical signals. The Doppler frequency shift between the directed ultrasound waves transmitted by the transmitter and the reflected ultrasound waves received by the receiver varies proportionally with the velocity of the moving acoustic target within the patient.

Figure 7:
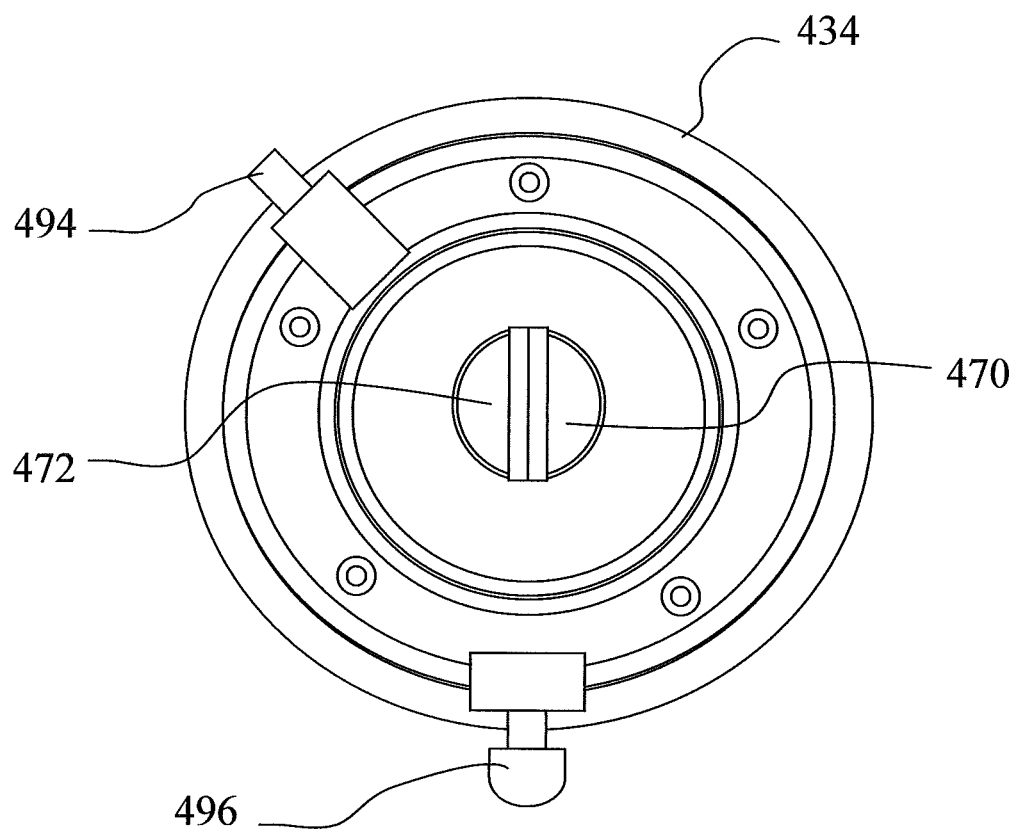
FIG. 7 is a bottom view of a stethoscope head in accordance with an embodiment of the present invention.
Figure 8:
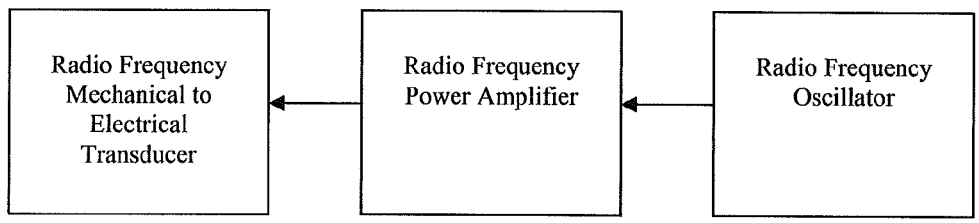
FIG. 8 is a schematic diagram illustrating a transmitter in accordance with an embodiment of the present invention.

As shown in FIG. 7, a stethoscope can include a head 434 comprising a transmitter 470. The transmitter 470 can generate an ultrasound signal that is mechanically transduced into the body of the patient. In one embodiment, as shown in FIG. 8, the transmitter 470 can comprise a sine wave oscillator with low harmonic content, and a power amplifier to drive the signal transducer. The transmitter 470 can be located at any location on the head 434 of the stethoscope capable of transmitting ultrasound signals into the body of the patient. In one embodiment shown in FIG. 12, the transmitter 470 is disposed adjacent a contact surface 482 for contacting the skin of a patient.

Figure 9:
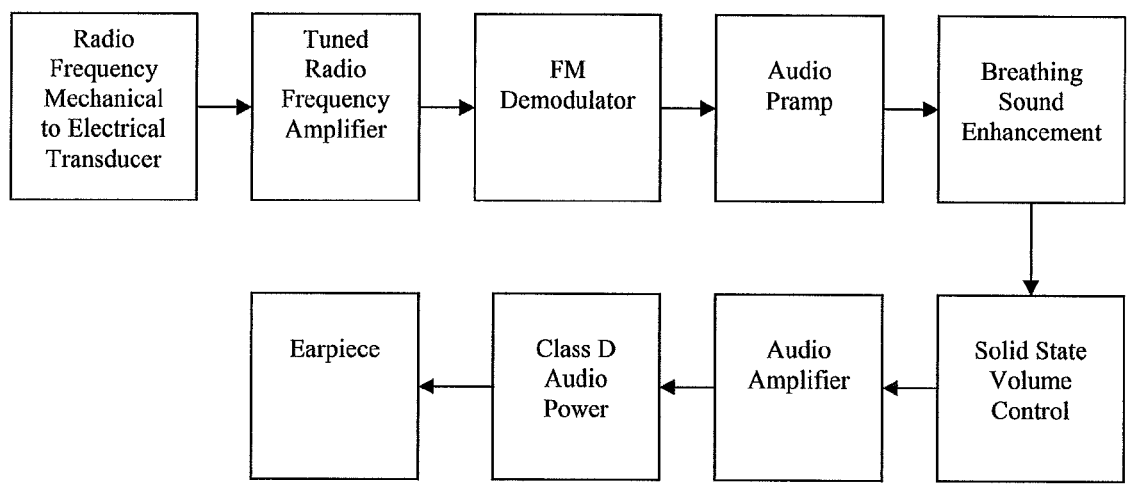
FIG. 9 is a schematic diagram illustrating a receiver in accordance with an embodiment of the present invention.

The transmitting element 470 and receiving element 472 may be canted inward slightly such that their beam patterns overlap over a depth range of interest in the body, for example, <1 in to ~6 inch. This involves placing the face of each element at a slight angle, for example, 1-5°, to the face of the stethoscope head with the outer edge of each element raised away from the face of the stethoscope head. Thus the transmitted acoustic beam points very slightly inward toward the axis perpendicular to the center of the stethoscope head, and waves reflected from surfaces parallel to the face of the stethoscope head are directed preferentially toward the receiving element rather than back to the transmitter. Note that both elements do not need to be angled inward so long as the angle between their two faces is maintained. Thus similar beam geometries and results can be achieved by locating one element (e.g., transmitter 470) parallel to the face of the stethoscope head and the other (e.g., receiver 472) canted inward at an angle to the face, for example 2-10°. Once the transmitted ultrasound signal encounters a moving surface within the patient, a reflected signal is generated that is received by the receiver 472 shown in FIG. 7. The receiver 472 can comprise any suitable structure capable of receiving reflected signals from the patient. Typically these are piezoelectric (PZT) sensing elements. In one embodiment, the receiver 472 is disposed within the head 434 of the stethoscope substantially adjacent the transmitter 470. The received signal is mixed with the transmitted carrier in an FM demodulator to produce a difference signal corresponding to the heart or lung motion. This is amplified and filtered as shown in FIG. 9.

Figure 10:
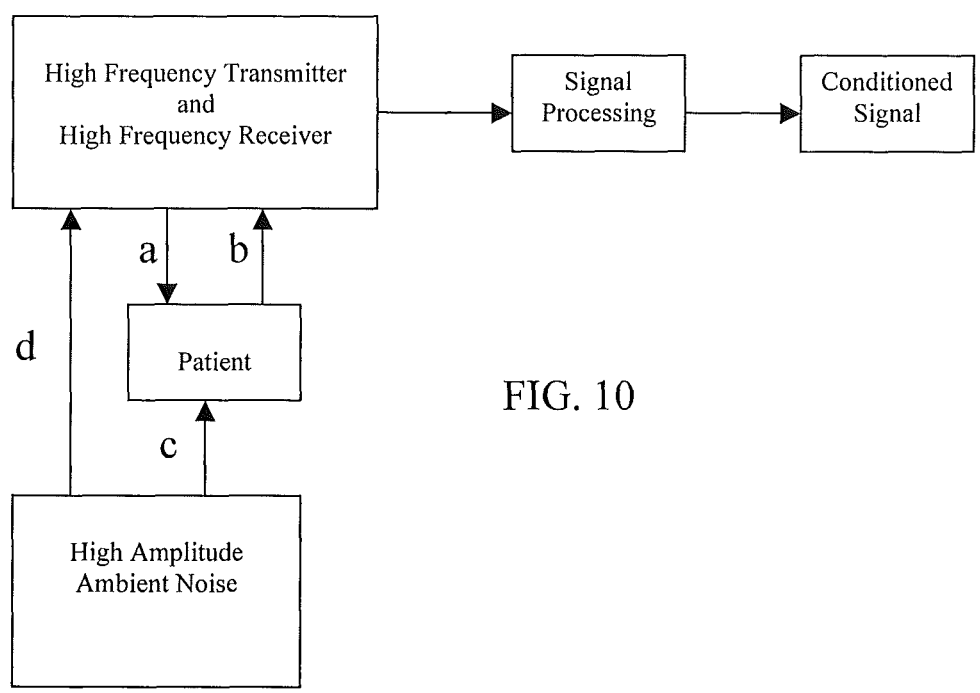
FIG. 10 is a schematic diagram illustrating the operation of an active Doppler stethoscope in accordance with an embodiment of the present invention.

A principle on which the Doppler relies for rejecting ambient noise is illustrated in FIG. 10. As described above, an ultrasound wave (a) on the order of 1-5 MHz is transmitted into the body, reflects off moving tissue/organ surfaces and returns (b) to the receiver with slightly changed frequency. For a traditional Doppler, the precise difference between transmitted and received frequencies is determined electronically and corresponds to the velocity of the moving surface. While this effect is useful, for example, in police radars for automobiles traveling in one direction through one medium (air) at relatively steady velocity, it is not optimum for observing heart and lung walls (constantly changing in velocity and direction) that are embedded in heterogeneous media (bones, fluids, muscle, fat, etc.). The feature of interest in the received signal is therefore not the static frequency delta but the variation in the frequency with time—or frequency modulation (FM). Accordingly, any one of a host of standard FM demodulation techniques can be employed to extract the desired time varying signal. In one such technique (known as slope detection) the received signal comprising the carrier, for example 2 MHz continuous wave ultrasound, plus its time varying Doppler shift components, is run through a very sharp filter on the input. The parameters of the filter may be set in such a way that its peak is close to but separated slightly from the transmit frequency, hence placing the transmit frequency at a very steep portion of the amplitude versus frequency curve. Accordingly, the desired Doppler frequency shifts (temporal variations in the received frequency compared to the steady state carrier) are converted to large amplitude changes on the carrier (amplitude modulation—AM). At this point any standard AM detector can be implemented to detect the baseline signal amplitude to strip out the carrier and leave just the modulation signal. This modulation signal is a measure of time varying frequency shifts and therefore corresponds to the desired time varying wall motions.

In the context of operating a Doppler device in high noise, as shown in FIG. 10, the received signal (h) arrives back at the receiver in competition with two sources of interference—background noise from the environment (d) arriving directly at the receiver from the air, and background noise/vibration induced in and transmitted through the patient to the receiver (c) along with the desired reflected ultrasound signal. In the above example FM demodulator, signal (d) is eliminated from the Doppler shift detector because its frequency is so low (typical background noise from a helicopter, for example, has a highest amplitude in the range of 50-2500 Hz) that it fails to pass through the sharp front end filter. Interfering signal (c) represents a quite different consideration because any anatomical motion excited by the vehicle vibration or airborne noise should be additive to lung and heart wall movements and therefore contribute to the "wall velocity" signal detected by the Doppler shift. In this case, signal (c) is swamped out by the desired wall motion signal because the vehicle vibrations and sounds are very low amplitude compared to the macroscopic movements of the outer walls of the heart and lungs. Hence, the Doppler shift is affected primarily by the latter.

While the above principles underlie the success of the device in detecting heart and lung activity in competition with external sources of interference, further refinement was required in the present invention to provide satisfactory operation in extremely high noise transport situations. Simple transmit/receive Doppler delivers a very noisy signal full of background crackling and artifacts caused by non-linear velocities of the organs being interrogated and inherent FM demodulator characteristics. In the presence of low FM signal levels, such as ultrasound reflections from moving tissue, any FM demodulator will interpret the background noise floor (in the electronics and in the medium under interrogation) as random frequency changes. These appear at the output as high amplitude noise and crackles. Elimination of these effects is therefore beneficial. Use of the Doppler in a noisy helicopter relies on the user's ability to manually increase the volume of the desired Doppler shift signal until it exceeds the background noise naturally leaking through the wearer's hearing protection and/or headset. If the Doppler signal is contaminated with artifacts and crackle then increasing the volume increases these competing sounds equally. Accordingly, in the present invention two filtering stages and a signal realism measure are introduced to produce a very clean, very pure signal corresponding only to the desired wall velocity. As described in the FM demodulator above, the first filter is applied on the front end of the ultrasound receiver to limit received signals to a very narrow band around the transmitted frequency thereby eliminating wide ranges of potential interfering signals from ever entering the receiver. For example, in one embodiment with a 2 MHz transmitter the receiver is limited to frequencies of 2 MHz+/−20 kHz. The second filter is applied on the output to the stethoscope headset and limits frequencies transmitted to the ear to the range of Doppler shifts expected from heart and lung wall velocities. Again this eliminates large bands of frequency corresponding to artifacts and other motions without physiological significance. This step also enables the sounds to be restricted to the region of maximum sensitivity of the human ear, for example 30 Hz to 10 kHz. The final tuning step in the Doppler mode is enhancing the apparent recognizability (or realism) of the signal to assist the medical professional or other user in identifying the source of the frequency shift. As mentioned before, the Doppler shift is a measure of wall velocity. Its frequency and tonal content has no inherent relationship to the underlying physiological process. The Doppler "sound" corresponding to the advancing and retreating outer surface of the heart bears almost no relation to the whooshing and fluid filling and clicking sounds that doctors hear from the heart with a standard acoustic stethoscope. The Doppler sound of the advancing and retreating pleura of the outer lung wall is not related in any straightforward way to the hissing rush of air through the bronchioles of the lungs or the cavity resonances observed by doctors. Subjective setting of bandpass filter limits is therefore helpful in making the Doppler wall motion sounds recognizable to the physician. Iterative adjustment of filter settings versus physician comments thus produces a signal that is not only audible above background leakage but readily identified with a physiological process.

Figure 11:
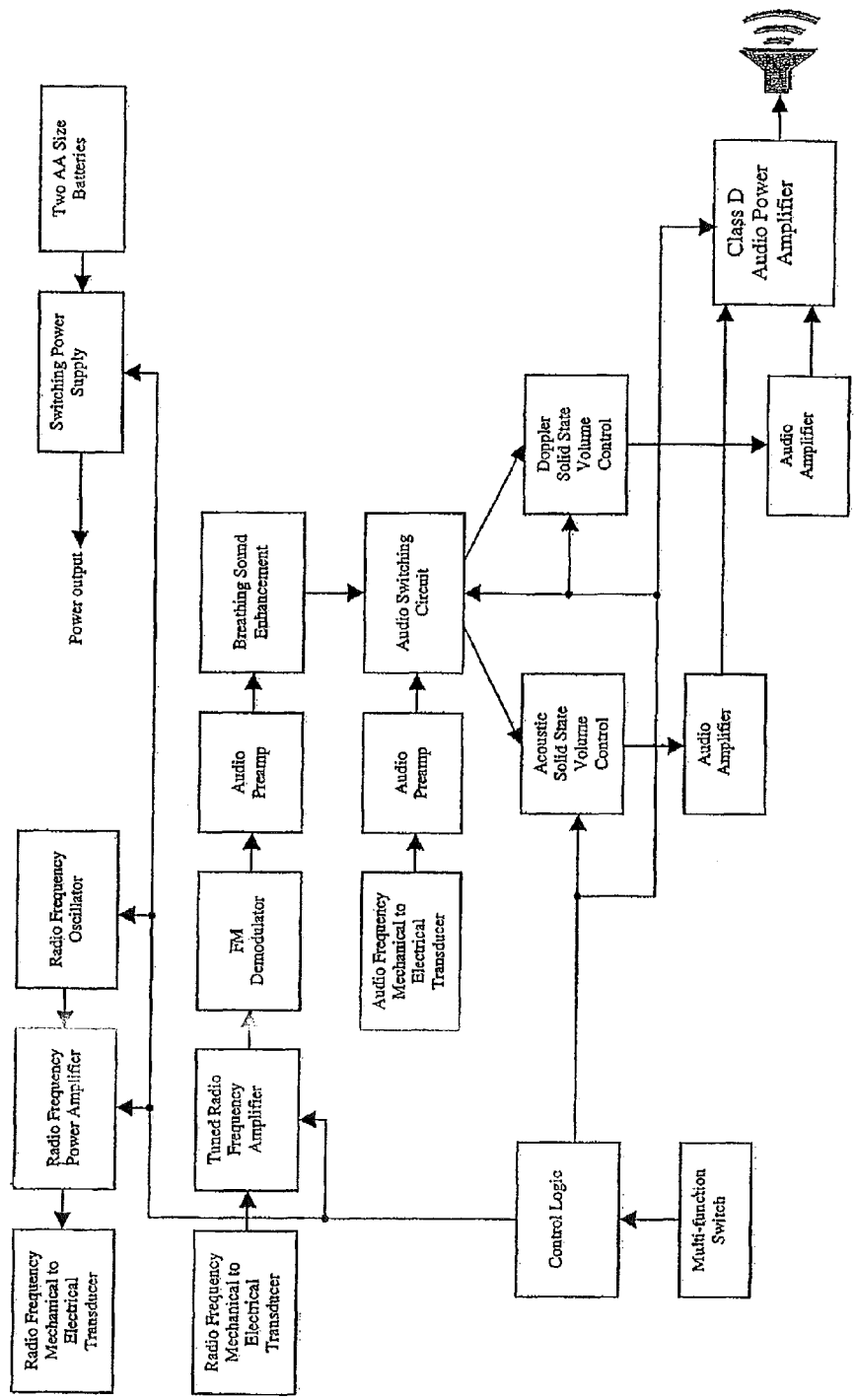
FIG. 11 is a schematic diagram illustrating the components of the electronics box shown in FIG. 1 in accordance with an embodiment of the present invention.

In a preferred embodiment, a passive acoustic system and an active Doppler system are combined in one stethoscope. The components of the electronics box 28 shown in FIG. 1 are schematically illustrated as shown in FIG. 11. As shown in FIG. 11, the components of the electronics box 28 can include a power supply, a multi-function switch and control logic, audio switching circuit, and a power amplifier. The power supply can be a high-efficiency, switch-mode boost power supply that supplies the power to the signal generation and conditioning circuitry. The control logic can consist of discrete static low voltage CMOS, which consume little power. In one embodiment, the control logic is powered directly from the power supply, such as a battery, and can be always on. This allows the control logic to control the power supply, stethoscope mode and volume controls, even when the power supply is off. This allows the user to set the mode of operation of the stethoscope. The mode of operation of the stethoscope determines which modality is employed by the operator. For example, the operator can select the mode of operation to include passive acoustic amplification or the operator can select the mode of operation to include transmit/receive Doppler detection. In certain situations, the operator of the stethoscope may find it desirable to transition from the passive acoustic mode to the active Doppler mode, and vice versa. In one embodiment, the operator can select the mode of operation of the stethoscope and the desired volume before turning the stethoscope on to eliminate high amplitude noise generated by rubbing contact with the patient. In one embodiment, the stethoscope can retain the previously used settings to minimize adjustment time. In another embodiment, the stethoscope may include a microcomputer in the control logic to enhance functionality.

In another embodiment, the audio switching circuit of the stethoscope of the present invention can be a logic-controlled analog switch used to gate the audio signal between the various function blocks, shown in FIG. 11, as required. The audio power amplifier can be any suitable amplifier, for example a high efficiency, high fidelity, Class D amplifier having a 1-watt output. This allows a high level of audio drive power with minimal wasted energy.

Figure 12:
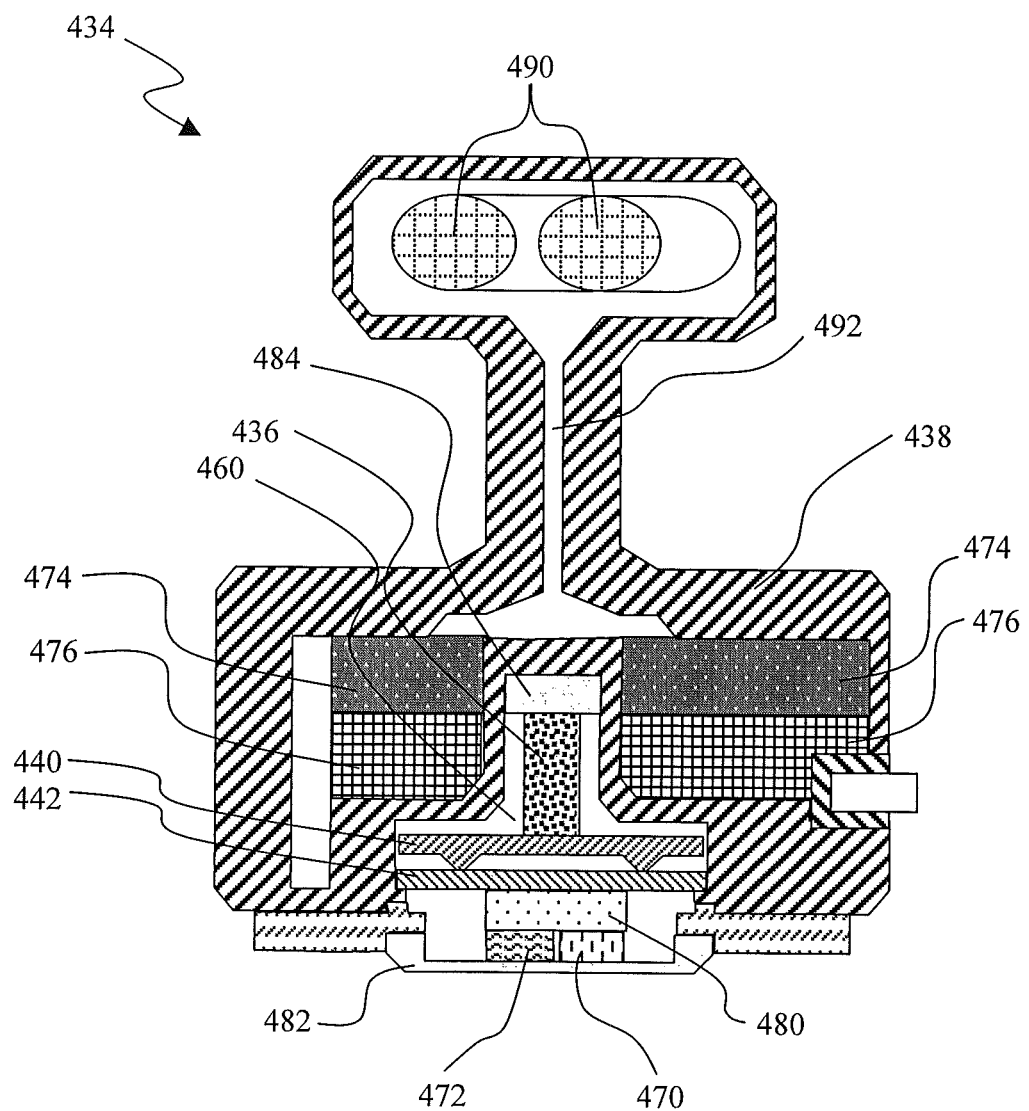
FIG. 12 is a partially schematic side sectional view of a stethoscope in accordance with an embodiment of the present invention.

In another preferred embodiment, the stethoscope head 434 shown in FIG. 12 can also include the components of a passive acoustic system, components of the active Doppler system, and all components of the signal processing control and power supply. As shown in FIG. 12, the stethoscope head 434 can comprise an electromechanical stack 436 disposed at least partially within the interior 460 of the housing 438. As described above, an end of the electromechanical stack 436 can be restrained against a rubber portion 484 positioned between an interior portion of the housing 460 and the electromechanical stack 436. Another end of the electromechanical stack 436 is engageable with a moveable piston 440 and/or a coupling plate 442 that are responsive to physiological signals, such as heartbeats and/or respiration of a patient.

In the Doppler mode, ultrasound signals may be transmitted by a thin disk of electromechanical material 470 and reflected signals are received by the receiver 472. The reflected signals are converted to electrical signals by the receiver 472 and input to signal conditioning circuits 474 and electrical interconnect boards 476 where they are filtered, amplified, demodulated, and further processed to enhance the detection of heart movement and/or lung movement associated with breathing. The electrical interconnect boards 476 and the signal conditioning circuits 474 can be connected to a power supply 490, such as a battery, through a channel 492 within the interior of the housing 438. The receiver 472 can comprise a signal transducer, which transmits to a narrow band tuned amplifier circuit. In one embodiment, an FM demodulator stage can be included in the circuitry to remove the carrier signal leaving only the audio frequency information corresponding to the movement of the anatomical structure under examination. This in turn can be followed by a preamp stage that provides both gain and an impedance change to provide the necessary signal conditioning for the following stage shown schematically in FIG. 11.

As shown in FIG. 12, a material 480, such as acoustically transparent ultrasound isolation foam, can be disposed in contact with the receiver 472. The stethoscope head 434 can include any suitable connector (not shown) for transmitting the processed signals to earpieces of the stethoscope. The head 434 can also include any suitable manual controls (not shown) for adjusting the mode, volume and filter of the signal. Although the passive acoustic amplification systems shown in FIGS. 2-4, 6 and 12 are directed to a system including an electromechanical stack, it is anticipated that other passive mechanical sound amplifying systems can be used in association with the present invention. Such systems that use PVDF, Terfernol, annealed metglas and other sensors can be envisaged with associated electronics that are suited to the material selected. For instance, PVDF will require electronics that can accommodate the low capacitance of the material; metglas will have to have electronics that monitor current output as opposed to voltage since this correlates with force in magnetic sensors.

It should be noted that the active Doppler and passive acoustic systems of the present stethoscope may be selected instantaneously with a simple electrical switch. Because the passive and active systems operate through the same "window", or outer face of the head of the stethoscope, there is no requirement to turn the stethoscope around or change an accessory to take advantage of the second mode. Accordingly, a sound that is detected in passive acoustic mode can immediately be interrogated for more information with the mode, or vice versa.

EXAMPLE 1

Figure 13:
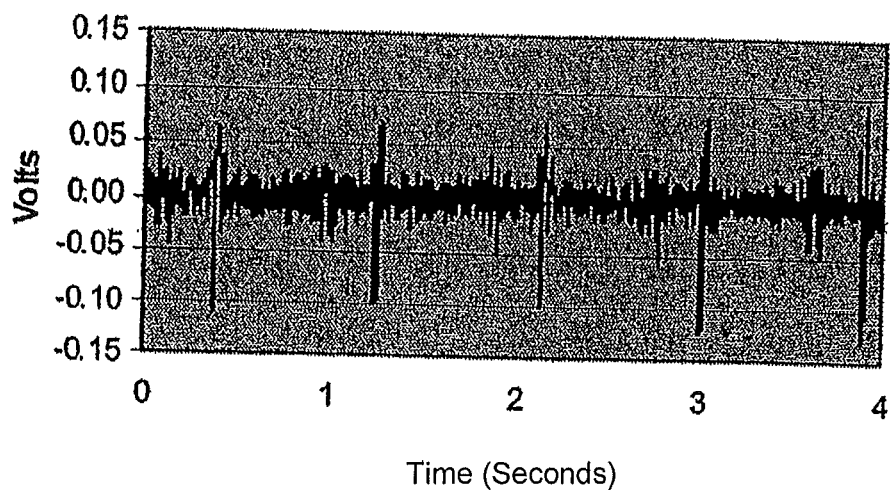
FIG. 13 is a graphical representation of several heartbeat signals sensed with a stethoscope over a background noise of 90 dBA in accordance with an embodiment of the present invention.
Figure 14:
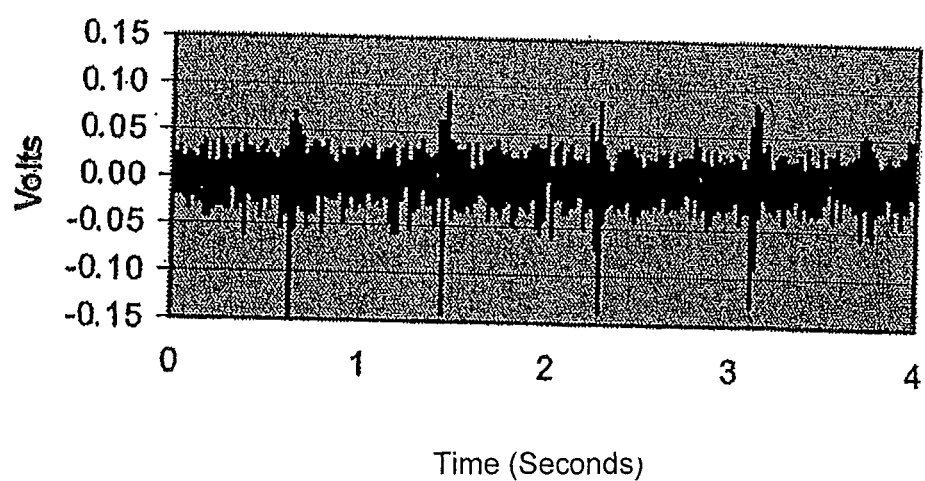
FIG. 14 is a graphical representation of several heartbeat signals sensed with a stethoscope over a background noise of 100 dBA in accordance with an embodiment of the present invention.

To test the effectiveness of the stethoscope of the present invention, a sound generation system was constructed using a signal generator, a B&K 2706 75-Watt amplifier, and a JBL #K120 speaker. Noise was generated in the band of 0.05-1.0 kHz from a recording of a Blackhawk UH-60 and its level was monitored by a conventional sound level meter set to "A" weighting. The sensor output at different noise levels was recorded using a 3562A HP Signal Analyzer and assessed subjectively by volunteers listening through headphones with CEP's placed under them. As shown in FIGS. 13 and 14, heartbeat sounds were recorded from the chest of a volunteer using the stethoscope of the present invention with 90 dBA and 100 dBA background noise levels respectively. Volunteers reported that they could hear heartbeats with both the 90 dBA and 100 dBA background noise. The electromechanical stack transducer of the stethoscope of the present invention has a relatively low capacitance (100 pF) and therefore offers very high electrical impedance at the low frequencies characteristic of physiological sounds. To match this to the signal conditioning electronics and hence maintain fidelity, the circuit has a very high input impedance. Accordingly, the stethoscope is optimized to capture the audible and sub-audible range down to about 10 Hz. The stethoscope frequency rolls off in the sub-sonic range below 10 Hz due to the characteristics of the transducer stack. It should be noted, however, that the time domain display in the above referenced figures does not accurately portray the frequencies coming out of the stethoscope below 20 Hz because of limitations in the audio recording device used in this experiment. Much of the heart signal comprises frequencies below 20 Hz, and thus the stethoscope output (as opposed to these visual displays) is an accurate depiction of these sounds.

EXAMPLE 2

Figure 15:
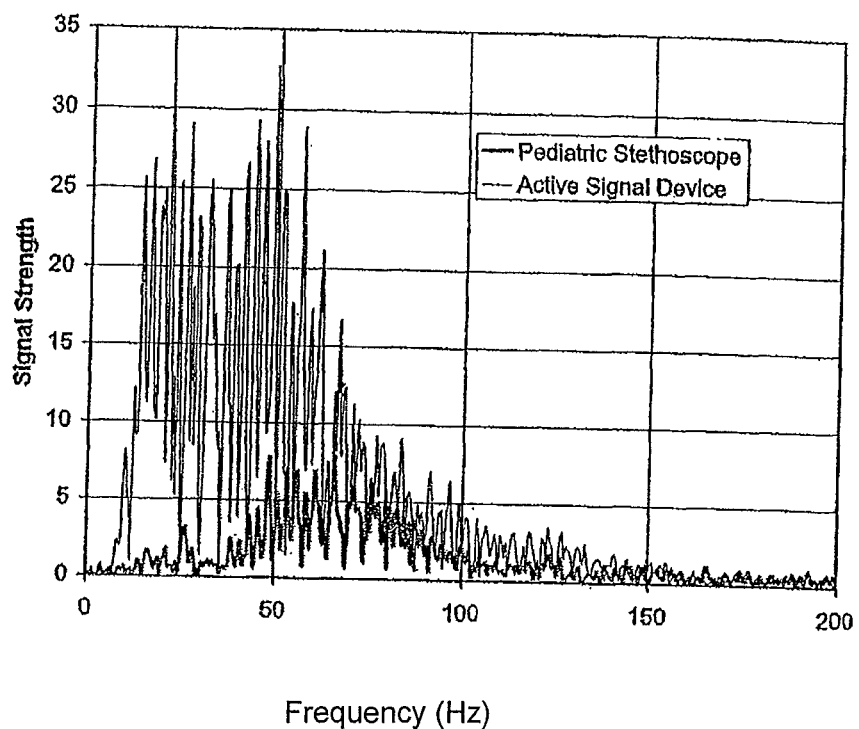
FIG. 15 is a graphical representation of neonate heart sounds sensed with a conventional pediatric stethoscope and sensed with a stethoscope in accordance with an embodiment of the present invention.

A stethoscope in accordance with the present invention was customized to the unique physiological and anatomical constraints of the pre-term infant. The device comprised a fingertip applied 10 mm diameter listening head with a solid state sensing element directly coupled to the baby's skin. The device was tested and its broadband high sensitivity was found to elucidate the most subtle of physiological sounds, some of which cannot be detected by a conventional pediatric stethoscope. An example of heart sounds recorded with the stethoscope described herein, identified as an Active Signal Device, and a conventional pediatric stethoscope is shown in FIG. 15. Subjectively, the clinician's perception of the heart sound was about the same for both devices, however, FIG. 15 shows that most cardiac acoustic information lies below about 150 Hz, and the stethoscope of the present invention produces 5-10 times the signal amplitude of the conventional stethoscope in this range. As shown in this example, the uniform response across the band of the present invention has a significant advantage over other conventional devices where the sensitivity rolls off at both higher and lower frequencies. Another advantage confirmed by this example is that clinicians have reported new previously inaudible sounds associated with heart motion and bowel peristalsis when the stethoscope of the present invention is used.

EXAMPLE 3

Figure 16:
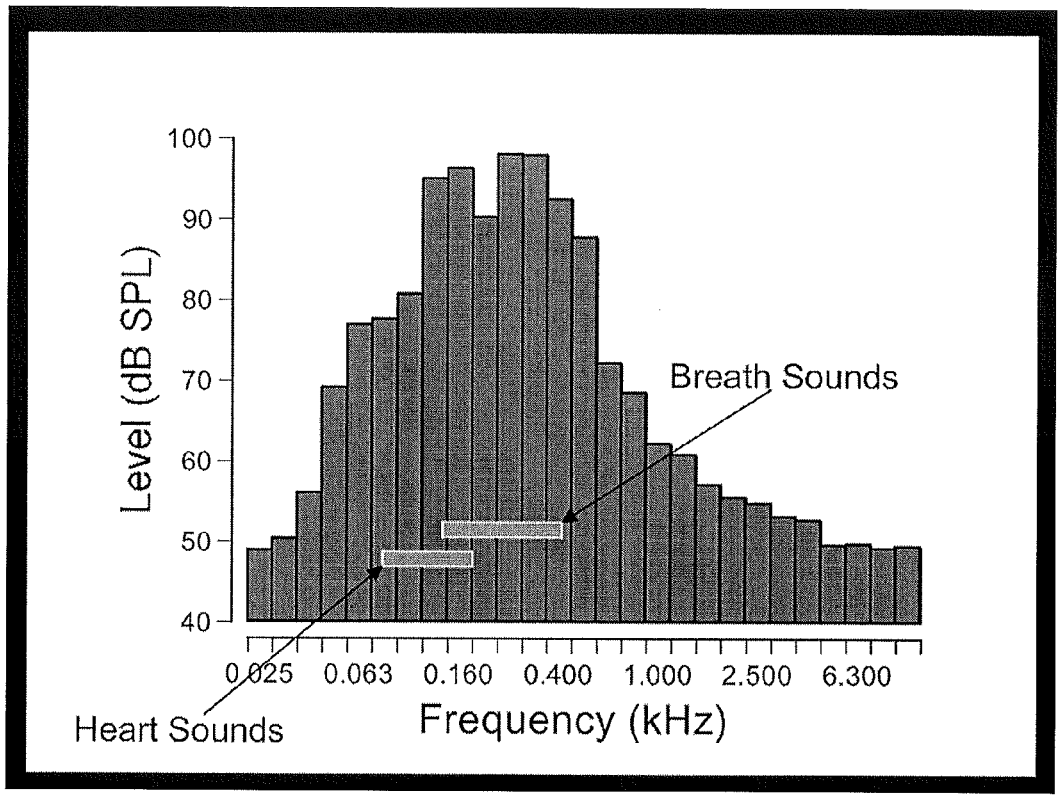
FIG. 16 is a bar chart illustrating the noise levels used in the reverberant sound chamber of Example 3, which was set up to replicate the typical spectrum of UH60 Blackhawk helicopter noise.
Figure 17:
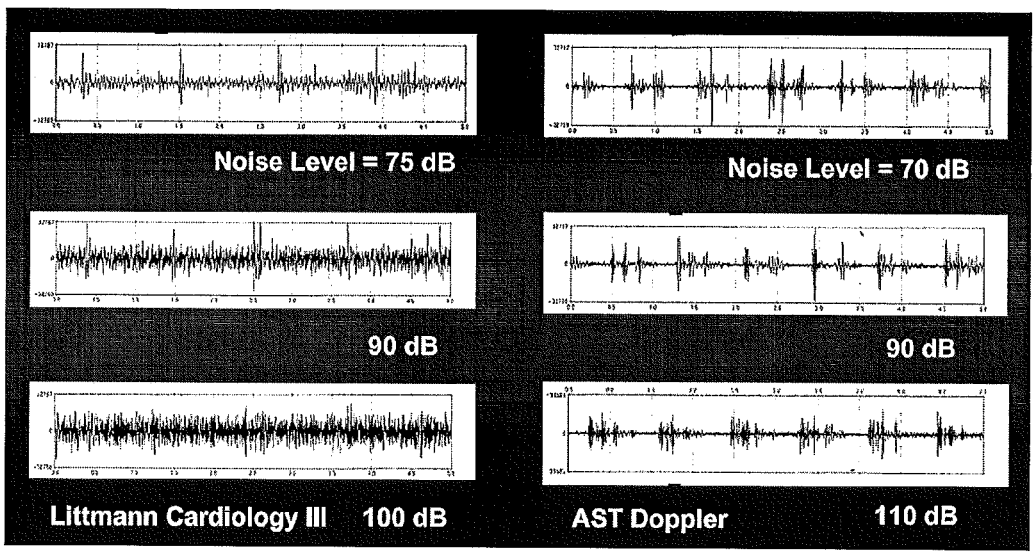
FIG. 17 is a series of charts illustrating digitally recorded examples of the output display from a conventional stethoscope and the Doppler stethoscope of the present invention.
Figure 18:
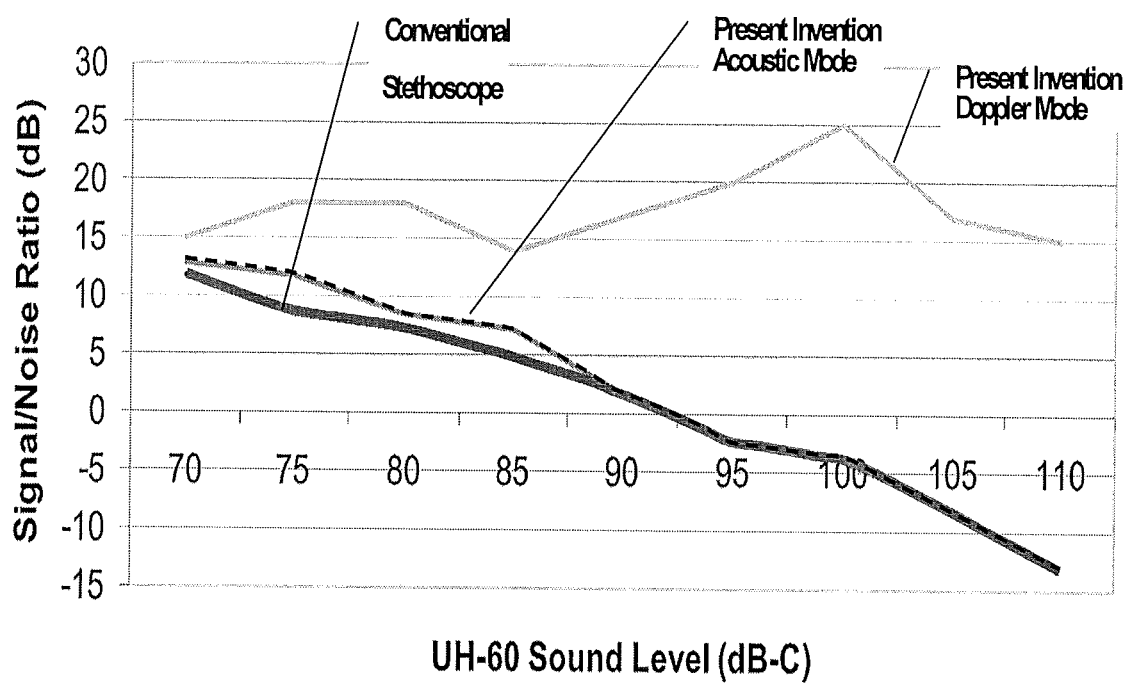
FIG. 18 is a chart illustrating signal to noise ratio for a conventional stethoscope, a passive embodiment of the present invention and an active Doppler embodiment of the present invention, as taken from the traces of Example 3, as the ratio of the signal amplitude during a heart beat compared to the noise level during the inter-beat interval.

An integrated acoustic/Doppler stethoscope in accordance with the present invention was comparison tested against a high quality conventional stethoscope (the Littmann Cardiology III) at the Acoustic Reverberation Chamber of the U.S. Army Aeromedical Research Laboratory (USAARL) at Ft. Rucker, Ala. under the direction of Dr. Adrianus Houtsma. The reverberant sound chamber was set up to replicate the typical spectrum of UH60 Blackhawk helicopter noise shown in FIG. 16. It can be seen that the frequency range of heart and breath sounds corresponds almost exactly to the highest amplitude portion of the helicopter noise spectrum explaining why conventional acoustic stethoscopes are defeated by this environment. The amplitude of the noise was increased successively from 70 to 110 dBA (the limit of the chamber) while a trained physician auscultated the heart sounds of a healthy volunteer using Army CEP ear plugs as combined ear protection and sound conduits. Concurrent with the physician's auscultation, the received signal was also digitally recorded for display and calculation purposes. Some representative examples of the output display from the conventional stethoscope and the Doppler stethoscope of the present invention are shown in FIG. 17. At relatively moderate noise levels (70-75 dBA) it can be seen that heart beat signals can be discerned at approximately 1 second intervals in the traces from both the conventional and Doppler stethoscopes. However, the signal is more clearly discriminated from the background noise in the Doppler. At 90 dBA the background noise becomes a much more significant fraction of the total signal for the conventional stethoscope while the Doppler heart beat signals remain just as far above the noise as at 70 dBA. At 100 dBA the heart beat signal is essentially lost in the background noise for the conventional stethoscope whereas the Doppler continues to pick up very clear signals far above the noise even at 110 dBA. Better quantification of these results was developed by examining all of the traces gathered during this series of experiments to calculate signal to noise S/N) ratios at each ambient noise level. Signal to noise was read off the traces as the ratio of the signal amplitude during a heart beat compared to the noise level during the inter-beat interval. FIG. 18 shows the results of this analysis. It can be seen that the signal to noise ratio for the Doppler remains for the most part well above 15 dBA all the way up to a background noise level of 110 dBA. Both the acoustic mode of the present stethoscope and the conventional stethoscope fail to detect the heart beat over the noise above about 92 dBA of background noise. The acoustic mode of the present invention shows an advantage of 2-4 dBA versus the conventional stethoscope but this advantage is lost above a background of 92 dBA.

The results obtained instrumentally and analytically in the above example were confirmed with subjective testing by physician evaluators in the same reverberation chamber. Volunteers' heart and breath sounds were monitored using the Doppler mode while the background noise level was increased from 90 dBA to 110 dBA, the limit of the chamber. Four physicians, including two flight surgeons, monitored several volunteers' and even at the highest levels both lung and heart sounds could be heard clearly enough to establish the proper function of each. Depending upon the person monitoring, the same auscultation was effective using a standard acoustic stethoscope up to approximately 80 dBA and using the integrated stethoscope in the passive mode up to ~95 dBA.

The usefulness of the extended frequency range provided by the present invention was shown in pediatric practice (see example 2) where previously inaudible sounds were now heard by the physician potentially enabling enhanced diagnosis of pediatric pathologies. Similarly, the device was tested on different patients with a collapsed lung (pneumothorax) in a trauma center. The wider frequency range of the present stethoscope revealed a high pitched whistle associated with the pneumothorax that had never before been heard with a conventional stethoscope. Similarly, during testing in a battalion aid station near Baghdad during the Gulf War an Army surgeon using this device was able to make a diagnosis of ventricular septal defect in a young Iraqi girl. The subtle murmur associated with this condition could easily have been missed in the noisy, bustling environment of this wartime field station.

Whereas particular embodiments of this invention have been described above for purposes of illustration, it will be evident to those skilled in the art that numerous variations of the details of the present invention may be made without departing from the invention as defined in the appended claims.

What is claimed is:

1. A stethoscope, comprising:
   a housing;
   a passive system incorporated into the housing, the passive system comprising an acoustic transducer;
   an active system incorporated into the housing, the active system comprising a transmitter and a receiver, wherein the transmitter generates high frequency signals which are reflected from an object thereby creating reflected high frequency signals having a frequency shift dependent on the motion of the object, and wherein the receiver detects the reflected high frequency signals and converts the high frequency signal into an electrical signal; and
   a switch in communication with the passive system and the active system, the switch able to select the passive system or active system.

2. The stethoscope of claim 1, wherein the acoustic transducer is an electromechanical stack.

3. The stethoscope of claim 1, wherein the acoustic transducer comprises at least one of piezoelectric lead zirconate titanate, quartz crystal, lithium niobates, barium titanate, lead titanate, meta-lead niobate, lead magnesium niobate, polyvinylidene di-fluoride, and/or Terfenol-D.

4. The stethoscope of claim 1, wherein the passive system is capable of detecting breathing and heartbeat of a patient with ambient noise levels above 85 dBA.

5. The stethoscope of claim 1, wherein the active system is capable of detecting breathing and heartbeat of a patient at ambient noise levels greater than 95 dBA.

6. The stethoscope of claim 1, wherein the active system is capable of detecting breathing and heartbeat of a patient at ambient noise levels up to at least 110 dBA.

7. The stethoscope of claim 1, wherein the switch is manually operable.

8. The stethoscope of claim 1, wherein the housing has a forward side and a rear side, wherein the passive system and active system are both oriented to receive input from the forward side.

9. The stethoscope of claim 1, further comprising an electronics box including a power supply, control logic, an audio switching circuit, a power amplifier and the switch.

10. A stethoscope capable of use in a high amplitude ambient noise environment, comprising:
    a housing having a face;
    an active system incorporated into the housing, the active system comprising a transmitter and a receiver adjacent to each other in the housing structured and arranged to send and receive ultrasonic signals through the face of the housing to and from a patient exposed to the high amplitude ambient noise environment; and
    a signal conditioner for reducing or eliminating unwanted signals selected from the high amplitude ambient noise and/or other spurious signals.

11. The stethoscope of claim 10, wherein the signal conditioner comprises a front end which receives the ultrasonic signals from the patient and wherein the front end comprises a demodulator.

12. The stethoscope of claim 11, wherein the ultrasonic signals are of a selected frequency and the demodulator comprises a bandpass filter set to pass only the ultrasonic signals within +/−1.0 percent of the selected frequency of the ultrasonic signals.

13. The stethoscope of claim 11, further comprising a bandpass filter following the demodulator which excludes demodulated signals outside an audible range.

14. The stethoscope of claim 13, wherein the audible range is restricted to about 40 Hz to about 500 Hz.

15. The stethoscope of claim 13, further comprising an amplifier to strengthen the demodulated and filtered signal and a user adjusted gain control.

16. A method for detecting anatomical structure motion in a patient in a high amplitude ambient noise environment comprising:
    transmitting a high frequency signal into the patient;
    receiving a reflected signal from the patient having a frequency shift dependent upon motion of the anatomical structure;
    demodulating the reflected signal;
    filtering the demodulated signal; and
    transmitting the filtered and demodulated signal to an earpiece.

17. The method of claim 16, further comprising amplifying the demodulated and filtered signal prior to the transmission to the earpiece.

18. The method of claim 17, further comprising adjusting the gain of the amplified signal prior to the transmission to the earpiece.

* * * * *